(12) United States Patent
Nguyen

(10) Patent No.: US 10,429,661 B2
(45) Date of Patent: Oct. 1, 2019

(54) RETROREFLECTOR DETECTORS

(71) Applicant: Sensors Unlimited, Inc., Princeton, NJ (US)

(72) Inventor: Thuc-Uyen Nguyen, Princeton, NJ (US)

(73) Assignee: Sensors Unlimited, Inc., Princeton, NJ (US)

( * ) Notice: Subject to any disclaimer, the term of this patent is extended or adjusted under 35 U.S.C. 154(b) by 43 days.

(21) Appl. No.: 15/671,539

(22) Filed: Aug. 8, 2017

(65) Prior Publication Data

US 2019/0049742 A1      Feb. 14, 2019

(51) Int. Cl.
| | | |
|---|---|---|
| *G02B 27/28* | (2006.01) | |
| *G02B 6/122* | (2006.01) | |
| *G02B 6/126* | (2006.01) | |
| *G02B 5/30* | (2006.01) | |
| *G02B 6/27* | (2006.01) | |
| *G01B 11/03* | (2006.01) | |
| *G01N 21/78* | (2006.01) | |
| *G01N 21/55* | (2014.01) | |

(52) U.S. Cl.
CPC ............ *G02B 27/283* (2013.01); *G01B 11/03* (2013.01); *G01N 21/55* (2013.01); *G01N 21/78* (2013.01); *G02B 5/3058* (2013.01); *G02B 6/122* (2013.01); *G02B 6/126* (2013.01); *G02B 6/2706* (2013.01)

(58) Field of Classification Search
CPC ...... G01B 11/03; G01N 21/78; G02B 5/3056; G02B 6/122; G02B 6/126; G02B 6/2706; G02B 27/286; G01S 7/4812; G01S 7/499; G01S 17/06
See application file for complete search history.

(56) References Cited

U.S. PATENT DOCUMENTS

| | | | |
|---|---|---|---|
| 5,114,226 A | | 5/1992 | Goodwin et al. |
| 5,374,991 A | * | 12/1994 | Atkinson ............... G01F 23/292 |
| | | | 356/493 |
| 5,530,549 A | | 6/1996 | Brown |
| 6,147,748 A | * | 11/2000 | Hughes .................. G01S 7/4812 |
| | | | 356/4.09 |
| 8,107,056 B1 | | 1/2012 | Riza |
| 9,395,174 B2 | | 7/2016 | Bridges |
| 9,631,922 B2 | | 4/2017 | Bridges et al. |

FOREIGN PATENT DOCUMENTS

| | | | | |
|---|---|---|---|---|
| EP | 1895266 A2 | * | 3/2008 | ........... G01B 11/002 |
| EP | 2157401 A1 | * | 2/2010 | ........... G01B 11/002 |
| EP | 2244055 A1 | * | 10/2010 | ........... G01B 11/002 |

* cited by examiner

*Primary Examiner* — Dominic J Bologna
(74) *Attorney, Agent, or Firm* — Locke Lord LLP; Scott D. Wofsy; Joshua L. Jones

(57) ABSTRACT

An optics arrangement includes a polarized beam splitter arranged along an collection axis, a first quarter waveplate arranged along the collection axis, and a second quarter waveplate. The second quarter waveplate is arranged along the collection axis and is optically coupled to the first quarter waveplate by the polarized beam splitter to limit return of polarized illumination originating in a scene being illuminated for retroreflector detection. Retroreflector detectors and methods of imaging a scene are also described.

17 Claims, 4 Drawing Sheets

RETROREFLECTOR DETECTORS

BACKGROUND OF THE INVENTION

1. Field of the Invention

The present disclosure relates to imaging devices, and more particularly to imaging devices and methods for detecting retroreflectors.

2. Description of Related Art

Retro-reflection is a property of a reflector whereby the reflector returns light or radiant energy incident upon the reflector along a reflection axis parallel to the axis along which the light or radiant energy was received. The returning energy provides information regarding the retroreflector including the spatial relationship of the retroreflector in a surrounding scene. A retroreflector detector can be employed to emit radiation and collect the returned radiation to detect the presence of retroreflectors in a scene.

Since retroreflector detection devices typically employ optical elements like lenses and windows that can reflect light received from a scene, some retroreflector devices can return a portion of the light received from the scene to the scene being imaged. While the amount of light is generally small, the returned light can limit the utility of retroreflector detection devices in some applications. For example, in applications where low observability is desirable such as on the battlefield, it can be necessary to limit observability by intermittently imaging the scene and masking the retroreflector between imaging intervals to limit observability. Intermittent use and masking reduces the likelihood that the retroreflector detection device be observed.

Such conventional methods and systems have generally been considered satisfactory for their intended purpose. However, there is still a need in the art for improved retroreflector detectors and methods of detecting retroreflectors. The present disclosure provides a solution for this need.

SUMMARY OF THE INVENTION

An optics arrangement includes a polarized beam splitter arranged along a collection axis, a first quarter waveplate arranged along the collection axis, and a second quarter waveplate arranged along the collection axis. The second quarter waveplate is optically coupled to the first quarter waveplate by the polarized beam splitter and is arranged to limit return of illumination reflected internally within a retroreflector imaging scene through the optics arrangement.

In certain embodiments, the optics arrangement can include an aperture plate. The aperture plate can be arranged along the collection axis. The first quarter waveplate can be arranged between the aperture plate and the polarized beam splitter along the collection axis. Collection optics can be arranged along the collection axis. The second quarter waveplate can be arranged between the collection optics and the polarized beam splitter along the collection axis.

In accordance with certain embodiments, the optics arrangement can include a collector. The collector can be arranged along the collection axis. The second quarter waveplate can be arranged between the collector and the polarized beam splitter along the collection axis. The collector can include a camera or a photodiode array. It is contemplated that the optics arrangement can include source optics.

It is also contemplated that, in accordance with certain embodiments, the source optics can be arranged along a source axis. The source axis can intersect the collection axis within the polarized beam splitter. The source axis can be orthogonal relative to the collection axis. The source optics can include a collimating element. The source optics can include a diverging element. An illuminator can be optically coupled to the polarizing beam splitter along the source axis. The illuminator can be arranged along the source axis. The illuminator can include a polarized laser optically coupled to the polarized beam splitter along the source axis. It is contemplated that the illuminator can include an optical fiber with an endface. The optical fiber endface can be orthogonal relative to the source axis. The optical fiber endface can be oblique relative to the source axis. The illuminator can be configured to provide illumination having a single polarization to the polarized beam splitter along the collection axis.

A retroreflector detector includes an optics arrangement as described above, an illuminator, and a collector. The illuminator is arranged along a source axis and source axis intersects the collection axis within the polarized beam splitter. A collector including a photodiode array is arranged along the collection axis with the second quarter waveplate arranged between the collector and the polarized beam splitter.

A method of imaging a scene includes receiving polarized illumination and transmitting the polarized illumination along an collection axis through first and second quarter waveplates optically coupled by a polarized beam splitter. Polarization of the transmitted illumination is flipped during transmission through one of the first and second quarter waveplates.

In certain embodiments, polarized illumination can be received at the polarized beam splitter prior to being transmitted through the first and second quarter waveplates. Polarized illumination can be received at the first quarter waveplate prior to being transmitted by the polarized beam splitter. Broadband illumination can be received through the first quarter waveplate at the polarized beam splitter. The polarized beam splitter can attenuate the broadband illumination, enhancing contrast between light reflected from the scene and optics in the scene. The polarized illumination can be reflected obliquely relative to the collection axis.

These and other features of the systems and methods of the subject disclosure will become more readily apparent to those skilled in the art from the following detailed description of the preferred embodiments taken in conjunction with the drawings.

BRIEF DESCRIPTION OF THE DRAWINGS

So that those skilled in the art to which the subject disclosure appertains will readily understand how to make and use the devices and methods of the subject disclosure without undue experimentation, embodiments thereof will be described in detail herein below with reference to certain figures, wherein.

DETAILED DESCRIPTION OF THE PREFERRED EMBODIMENTS

Figure 1:
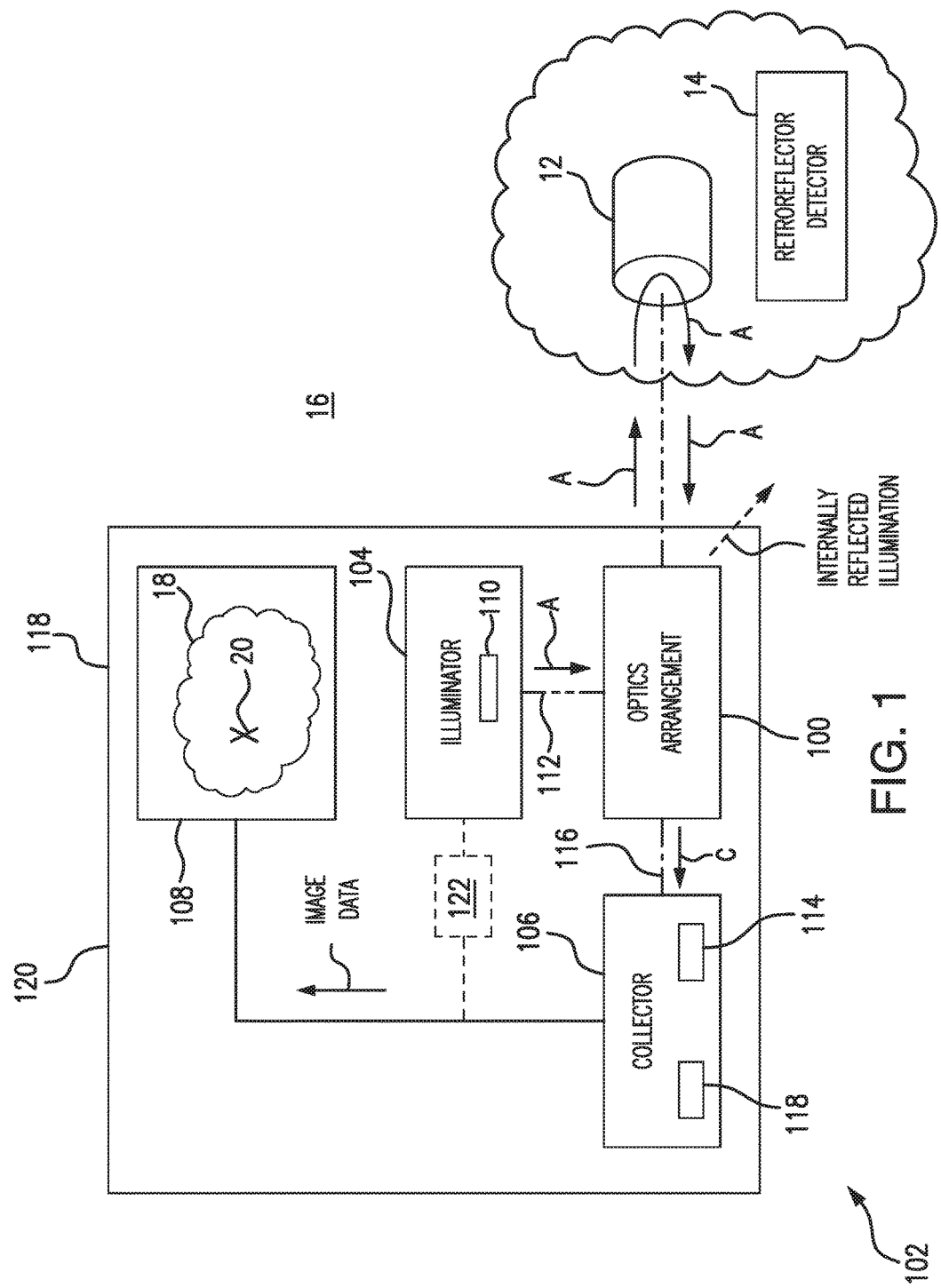
FIG. 1 is a schematic view of an exemplary embodiment of a retroreflector detector, showing an optics arrangement with low observability imaging a scene with a retroreflector and a retroreflector detector.

Reference will now be made to the drawings wherein like reference numerals identify similar structural features or aspects of the subject disclosure. For purposes of explanation and illustration, and not limitation, a partial view of an exemplary embodiment of an optics arrangement in accordance with the disclosure is shown in FIG. 1 and is designated generally by reference character 100. Other embodiments of optics arrangements, retroreflector detectors, and imaging methods in accordance with the disclosure, or aspects thereof, are provided in FIGS. 2-4, as will be described. The systems and methods described herein can be used for detecting retroreflectors while limiting the observability of the optics arrangement being used to detect the retroreflectors, such as when imaging a battlefield to detect the optics of an unfriendly weapon system like a sniper's scope, though the present disclosure is not limited to battlefield applications or to retroreflector detection in general.

Referring to FIG. 1, a retroreflector detector 102 is shown. Retroreflector detector 102 includes optics arrangement 100, an illuminator 104, a collector 106, and a user interface 108. Illuminator 104 is configured to generate polarized illumination A and provide polarized illumination A to optics arrangement 100. It is contemplated that illuminator 104 include a polarized laser source 110 configured to generate polarized illumination having a selected polarization, e.g., vertical, horizontal, +/−45 degrees, etc., as suitable for an intended application. Illuminator 104 is configured to generate polarized illumination within a selected waveband, such as an infrared, a near-infrared (NIR), a shortwave-infrared (SWIR), a mid-range infrared (MWIR), and/or a long-wave (LWIR) waveband. Although described herein as employing a polarized laser 112, it is to be understood and appreciated that other polarized light sources can be employed such as a non-polarized laser, lamp or light-emitting diode, and remain within the scope of the present disclosure.

Optics arrangement 100 is arranged to receive polarized illumination A, direct polarized illumination A to a scene 10, and receive from a retroreflector 12 disposed within scene 10 reflected polarized illumination A. In this respect optics arrangement 100 is optically coupled to illuminator 104 along a source axis 112 to receive polarized illumination A. Optics arrangement 100 is also arranged to receive reflected polarized illumination A from a scene 10 with low observability (shown with dashed arrow), meaning that relatively little (or substantially none) of internally reflected illumination received from scene 10 returns to scene from optics arrangement 100. As will be appreciated by those of skill in the art in view of the present disclosure, limiting (or eliminating) the return of internally reflected illumination to scene 10 limits the ability of retroreflector devices in scene 10, e.g., unfriendly retroreflector device 14, to detect the presence of retroreflector detector 102 during time intervals that retroreflector detector 102 is imaging scene 10.

Collector 106 is configured to receive reflected illumination C from optics arrangement 100 and generate image data from reflected illumination C. Collector 106 is optically coupled to optics arrangement 100 along a collection axis 116 and includes a photodiode array 114. Photodiode array 114 is configured to respond to reflected illumination within a selected waveband incident upon photodiode array 108 and generate therefrom image data. The selected waveband to which photodiode array 114 is responsive can include one or more of a visible, an infrared, a NIR, a SWIR, an MWIR, and/or an LWIR waveband. Examples of suitable photodiode arrays include those available from Sensors Unlimited Incorporated, of Princeton, N.J. Although described herein as having a photodiode array 114, it is to be understood and appreciated that collector 106 can alternatively (or additionally) include a camera 118, as suitable for an intended application.

User interface 108 is communicative with collector 106 to receive therefrom image data and generate an image 18 of scene 10. When image data provided to user interface 108 includes information indicative of the presence of retroreflector 12 in scene, user interface further displays an indication 20 of the retroreflector within image 20 of scene 10, thereby alerting a user to the presence of retroreflector 12 in scene 10. In the illustrated exemplary embodiment user interface 108 is integrally housed with optics arrangement 100 in a common housing 120, which can be scope for a weapons system like a rifle. As will be appreciated by those of skill in the art in view of the present disclosure, user interface 108 can alternatively be remote from retroreflector detector 102, such as through a communications link (not show for clarity reasons) configured to covey the image data to a user interface location remote from a location of retroreflector detector 102.

In certain embodiments retroreflector detector 102 can include a controller 122. Controller 122 can be operatively connected to illuminator 104 and collector 106 and configured to cause illuminator 104 to provide illumination A to optics arrangement 100, receive image data from collector 106 including information relating to scene 10, and provide image 18 to a user via user interface 108 in conjunction with analysis and exploitation, as appropriate for a given application. Controller 122 can include either or both of circuitry and/or software and implanted to respond to instructions to execute the instructions, such as imaging method 200 (shown in FIG. 4).

Figure 2:
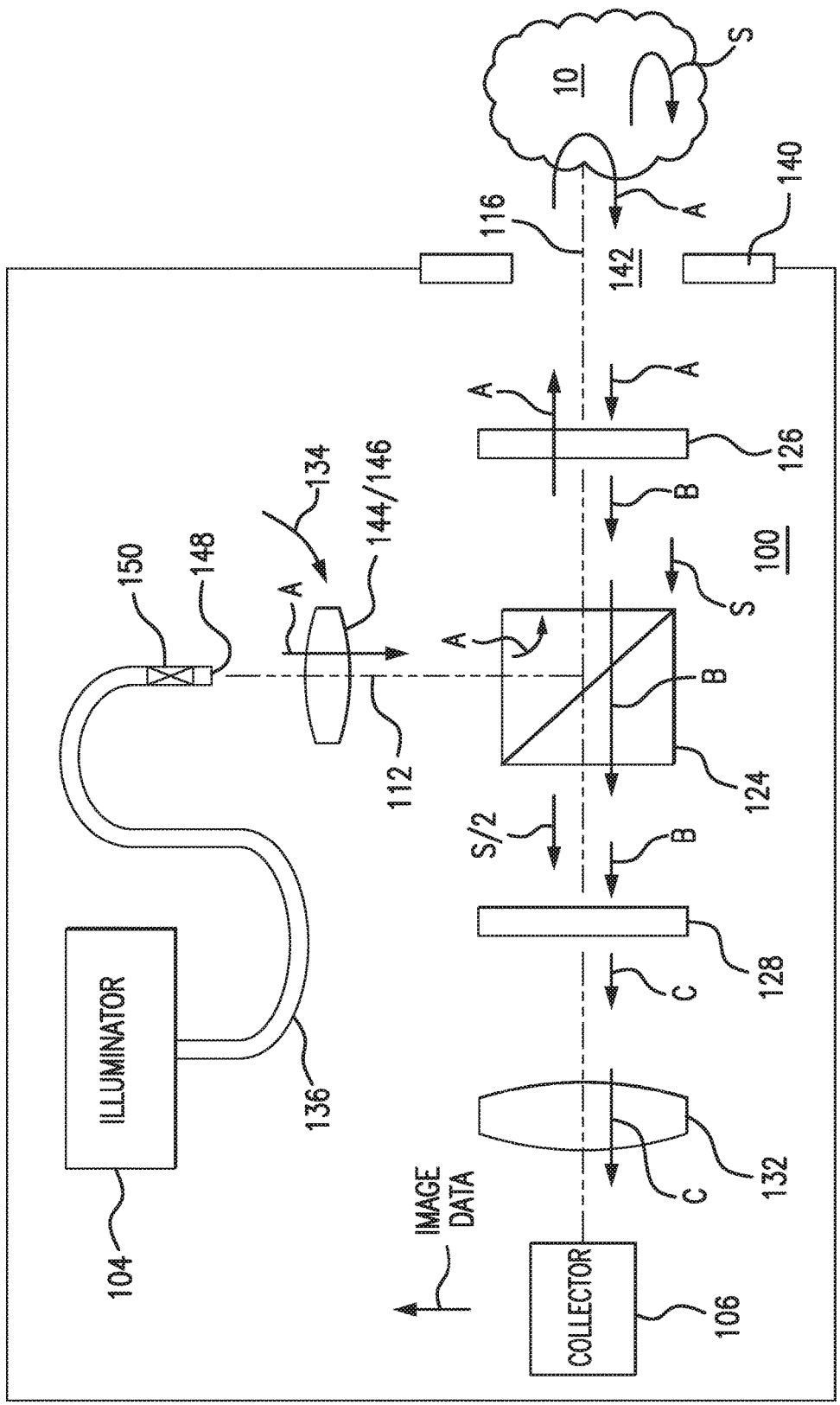
FIG. 2 is a schematic view of the retroreflector optics arrangement shown in FIG. 1, showing the optics arrangement reflecting and transmitting light between an illuminator and a collector for detecting a retroreflector in a scene being imaged by the retroreflector detector.

With reference to FIG. 2, optics arrangement 100 is shown. Optics arrangement 100 includes polarized beam splitter 124, a first quarter waveplate 126, and a second quarter waveplate 128. Optics arrangement 100 also includes an aperture plate 130, one or more source optic 132, and one or more collector optic 134. In the illustrated exemplary embodiment an optics arrangement 100 additionally includes an optical fiber 136.

Illuminator 104 is optically coupled to polarized beam splitter 124 along optical axis 112 by optical fiber 136. Optical fiber 136 has an end face 148 that is fixed relative to polarized beam splitter 124 by a connector 150. In the illustrated exemplary embodiment end face 148 is arranged orthogonally relative to optical axis 112 and is fixed by an ultra-physical contact (UPC) connector 150. Use of a UPC connector can reduce the space occupied by optical arrangement 100, reducing size of housing 120 (shown in FIG. 1) containing optical arrangement 100.

The one or more source optic 134 are arranged along source axis 112 between illuminator 104 and polarized beam splitter 124. In the illustrated exemplary embodiment source the one or more source optic 134 is arranged between optical fiber 136 and polarized beam splitter 124 along source axis 112. The one or more source optic 134 can include a diverging lens 144 or a collimating lens 146, as suitable for an intended application.

Polarized beam splitter 124 is arranged along source axis 112 and collection axis 116. Source axis 112 intersects collection axis 116 within polarized beam splitter 124 and is orthogonal to collection axis 116. Polarized beam splitter 124 is matched to the polarization of illuminator 104 such that at least a portion of polarized illumination received by polarized beam splitter 124 along source axis 112 is reflected by polarized beam splitter 124, the received polarized illumination thereby be directed by polarized beam splitter 124 towards scene 10. In certain embodiments substantially all polarized illumination A generated by illuminator 104 is reflected along collection axis 116 and towards scene 10 by polarized beam splitter 124.

First quarter waveplate 126 is arranged along collection axis 116 between polarized beam splitter 124 and scene 10. First quarter waveplate 126 is arranged to transmit, without changing polarization, polarized illumination A incident upon a surface of first quarter waveplate 126 facing polarized beam splitter 124. First quarter waveplate 126 is also arranged to transmit illumination reflected scene 10, i.e. reflected polarized illumination B, reflected from scene 10 by a retroreflector located in scene 10, e.g., retroreflector 12 (shown in FIG. 1). First quarter waveplate 126 is further arranged to flip polarization of illumination reflected from scene 10 incident upon a surface facing scene 10, transmitting the reflected illumination with flipped polarization as illumination B along collection axis 116. Illumination B, having its polarization flipped, is transmitted by polarized beam splitter 124 along collection axis 116.

Second quarter waveplate 128 is arranged along collection axis 116 and on side of polarized beam splitter 124 opposite first quarter waveplate 126. In this regard second quarter waveplate 128 is optically coupled to first quarter waveplate 126 by polarized beam splitter 124. Second quarter waveplate 128 is configured to transmit reflected illumination B along collection axis 116, second quarter waveplate 128 flipping polarization of reflected illumination B incident upon a surface of second quarter waveplate 128 facing polarized beam splitter 124 and transmitting the illumination as reflected illumination C to collector 106. Collector 106 responds to incident illumination C by generating image data, which is conveyed to user interface 108 (shown in FIG. 1).

The one or more collector optic 132 is arranged along collection axis 116. Collector optic 132 is arranged along collection axis 116 on a side of second quarter waveplate 128 opposite polarized beam splitter 124. Collector optic 132 optically couples collector 106 to second quarter waveplate 128, and therethrough to polarized beam splitter 124 and first quarter waveplate 126 for imaging scene 10.

In the illustrated exemplary embodiment an aperture plate 140 is arranged along collection axis 116. Aperture plate 140 has an aperture 142 through which scene 10 is optically copulated to polarized beam splitter 124, and therethrough to collector 106. Aperture 142 can include a window or other transmissive optical element, as suitable for an intended application.

As will be appreciated by those of skill in the art, illumination from sources other than illuminator 104 can enter retroreflector detector 102. For example, while imaging during daylight conditions sunlight reflected from scene 10 can enter retroreflector detector 102. In bright conditions, sunlight can mask the presence of a retroreflector image by washing out indication of the retroreflector in the image. To mitigate the effect of such ambient illumination, polarized beam splitter 124 is arranged to selectively attenuate ambient illumination S more heavily than reflected polarized illumination B. In certain embodiments, polarized beam splitter 124 attenuates ambient illumination S by about 50%. Selective attenuation of ambient illumination S enhances the contrast between indicator 20 (shown in FIG. 1) and image 18 (shown in FIG. 1), thereby making retroreflector more readily discernable in scene 10.

Figure 3:
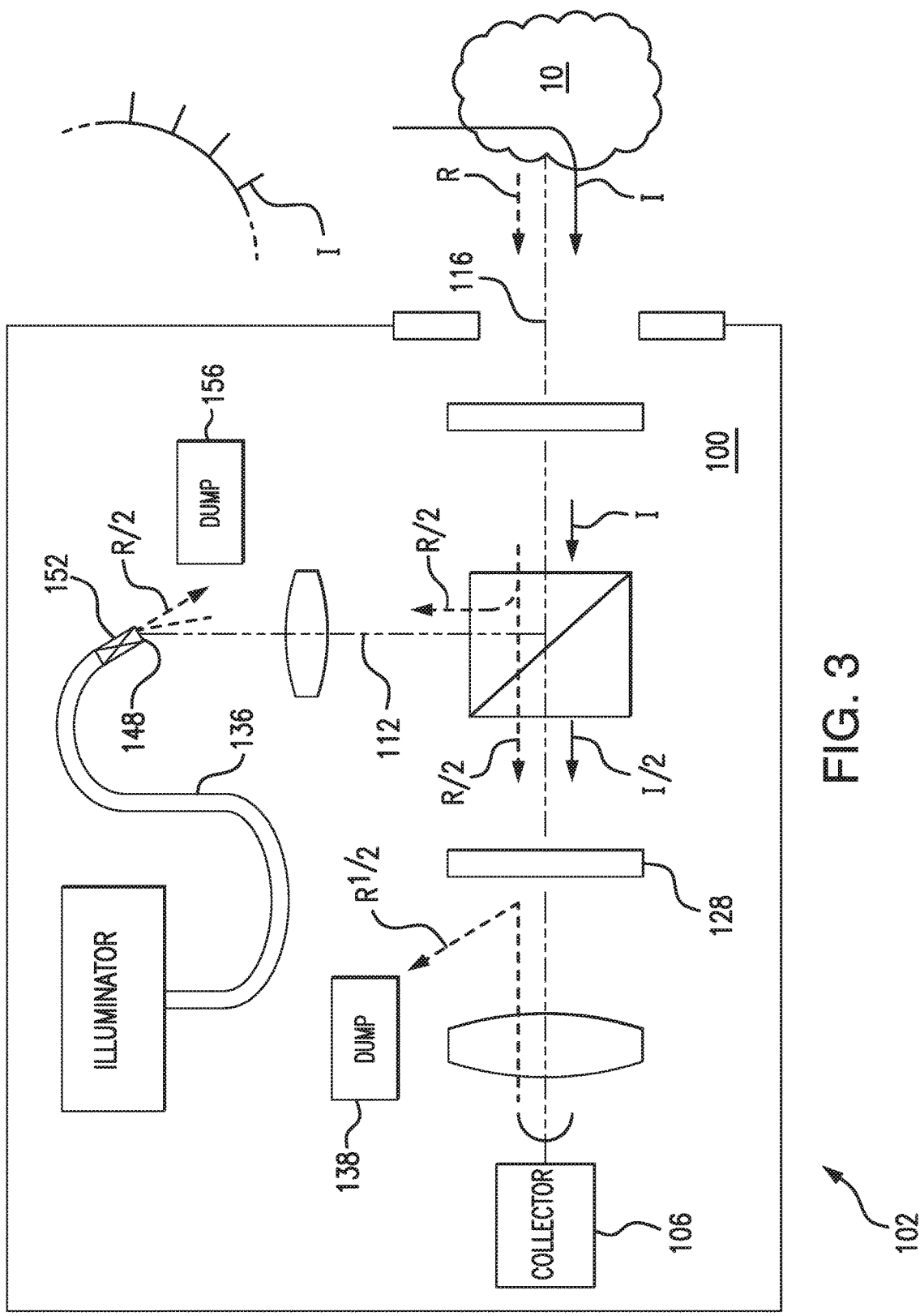
FIG. 3 is a schematic view of the retroreflector optics arrangement of FIG. 1, showing a contrast enhancement feature and low observability features of the retroreflector optics arrangement.

With reference to FIG. 3, low observability of optics arrangement 100 is shown. As will be appreciated by those of skill in the art in view of the present disclosure, detecting optics, e.g., unfriendly retroreflector detector 14 (shown in FIG. 1), without being detected can improve survivability of retroreflector detector 102. Since retroreflector detector devices, e.g., unfriendly retroreflector detector 14, generally detect retroreflector detectors by emitting illumination and analyzing reflected illumination reflected by optical elements of retroreflector detectors like retroreflector detector 102, retroreflector detector 102 is configured to reduce illumination reflected to scene 10 by optics arrangement 100, thereby providing low observability.

For example, polarized beam splitter 124 splits illumination R received from retroreflector detector 14 (shown in FIG. 1) according to polarization. In this respect about one-half of illumination R with a first polarization (shown in FIG. 3 with a dashed arrow R/2 oriented along source axis 112) is reflected by polarized beam splitter 124 along source axis 112, and about one-half of illumination R (shown in FIG. 3 with a dashed arrow R/2 oriented along collection axis 116) having a second polarization is transmitted along collection axis 116 towards collector 106.

Illumination R/2 having the second polarization is transmitted by polarized beam splitter 124 along collection axis 116 to second quarter waveplate 128. Second quarter waveplate 128 flips polarization of illumination R/2 and transmits illumination R/2 with flipped polarization to collector 106. Collector 106 reflects illumination R/2 with flipped polarization to a surface of second quarter waveplate 128 facing collector 106. Second quarter waveplate 128 absorbs and/or reflects illumination R/2 with flipped polarization, for example by directing illumination R/2 with flipped polarization to a dump 138. As will be appreciated, directing illumination R/2 with flipped polarization to dump 138 deprives retroreflector detector 14 (shown in FIG. 1) of the illumination, making retroreflector detector 102 less observable than would otherwise be the case. It is contemplated that dump 138 can include a detector, which can provide a signal to user interface 108 (shown in FIG. 1) distinguishing retroreflector detector 14 from other retroreflectors present in scene 10.

Illumination R/2 having the first polarization is reflected by polarized beam splitter 124 along source axis 112 to optical fiber 136. Reflected illumination 30 with the first polarization travels along source axis 112 to end face 148. As will be appreciated by those of skill in the art in view of the present disclosure, the end face of an optical fiber, regardless of how small, can reflect illumination along the axis from which it was received. As will also be appreciated by those of skill in the art in view of the present disclosure, such reflection can be discerned by unfriendly retroreflector detectors, e.g., retroreflector detector 14 (shown in FIG. 1).

To make illumination R/2 with first polarization unavailable to unfriendly retroreflector devices end face 148 of optical fiber 136 is oblique relative to source axis 112. In this respect an angled-proximity contact (APC) connector 152 fixes optical fiber 136 relative to optical axis 112 such that end face 148 is oblique relative to source axis 112. The angle of end face 148 is such that illumination R/2 with first polarization is directed at an angle oblique relative to source axis 112. In the illustrated exemplary embodiment the oblique orientation of end face 148 directed illumination R/2 towards a dump 156, which absorbs illumination R/2, thereby preventing return of illumination R/2 from optics arrangement 100 to scene 10. Dump 156 can include a detector for providing a signal to user interface 108 (shown in FIG. 1) distinguishing retroreflector detector 14 from other retroreflectors present in scene 10.

Figure 4:
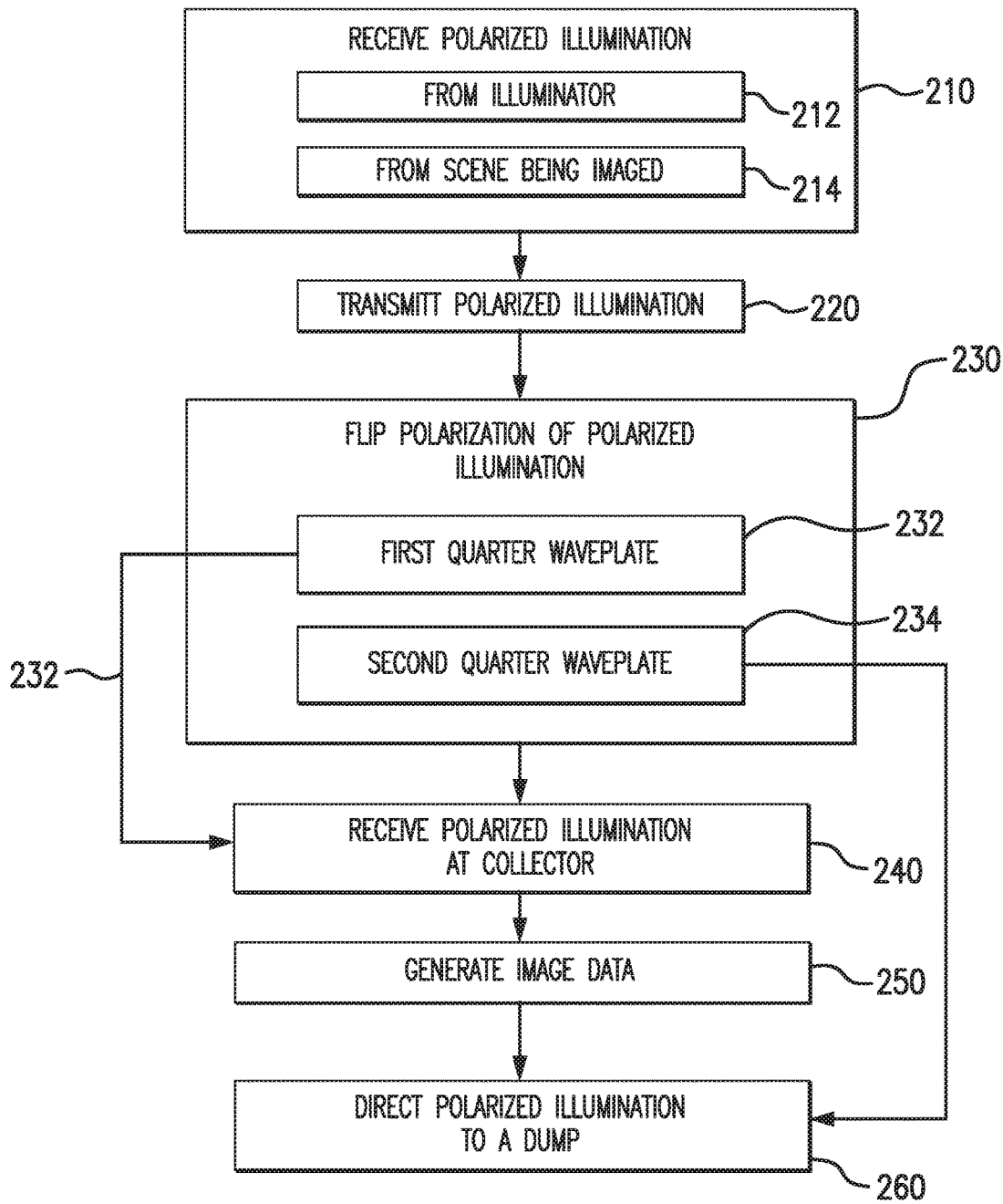
FIG. 4 is a block diagram of a method of imaging a scene with a retroreflector device while limiting the observability of the retroreflector device, showing the steps of the method.

With reference to FIG. 4, an imaging method 200 is shown. Imaging method 200 includes receiving polarized illumination, as shown with a box 210. The polarized illumination can be received from an illuminator, e.g., illuminator 104 (shown in FIG. 1), as shown with box 212. The polarized illumination can be received from a scene, e.g., scene 10 (shown in FIG. 1), as shown with box 212. The polarized illumination is transmitted along a collection axis, e.g., collection axis 116 (shown in FIG. 1), as shown with box 220. It is contemplated that the illumination be transmitted along the collection axis through one or more quarter waveplates, e.g., first quarter waveplate 126 (shown in FIG. 2) and second quarter waveplate 128 (shown in FIG. 2). It is also contemplated that the polarized illumination be transmitted, at least in part, and reflected, at least in part, by a polarized beam splitter optically coupled to the first quarter waveplate and the second quarter waveplate, e.g., polarized beam splitter 124 (shown in FIG. 2).

Polarization of the polarized illumination is flipped according to the origin of the polarized illumination, as shown with box 230. For example, polarization of illumination originating from the retroreflector detector is flipped in the first quarter waveplate, as shown with box 232. The polarized illumination is thereafter reflected from the scene and transmitted to a collector, e.g., collector 106 (shown in FIG. 1), as shown with box 240 and arrow 236. The collector 106 generates image data from the polarized illumination.

When the polarized illumination originates from the scene being imaged polarization of the polarized illumination is flipped in the second quarter waveplate, as shown with box 234. This causes the second quarter waveplate to absorb or reflect the polarized illumination off the collection axis, as shown with arrow 238. The polarized illumination can thereafter be directed to a dump, e.g., dump 138 and/or dump 158 (shown in FIG. 3).

The methods and systems of the present disclosure, as described above and shown in the drawings, provide for imaging systems, retroreflector detectors, and methods of imaging scenes with superior properties including retroreflector detection with low observability. In certain embodiments the present disclosure can provide covert retroreflector devices in a defensive setting, for example, when it is desirable to detect optics located in the field of view without exposing the position of the retroreflector detector device to detection. For example, when searching for an enemy's rifle scope in the field it can be desirable to avoid giving away the location of the retroreflector detector, such as when the retroreflector is located with the optics of a friendly weapons system. While the apparatus and methods of the subject disclosure have been shown and described with reference to preferred embodiments, those skilled in the art will readily appreciate that change and/or modifications may be made thereto without departing from the scope of the subject disclosure.

What is claimed is:

1. An optics arrangement, comprising:
    a polarized beam splitter arranged along an collection axis;
    a first quarter waveplate arranged along the collection axis;
    a second quarter waveplate arranged along the collection axis, wherein the second quarter waveplate is optically coupled to the first quarter waveplate by the polarized beam splitter to limit return of polarized illumination originating in a scene being illuminated for retroreflector detection; and
    a collector arranged along the collection axis, wherein the second quarter waveplate is arranged between the collector and the polarized beam splitter along the collection axis.

2. The optics arrangement as recited in claim 1, further comprising an aperture plate arranged along the collection axis, wherein the first quarter waveplate is arranged between the aperture plate and polarized beam splitter along the collection axis.

3. The optics arrangement as recited in claim 1, further comprising collection optics arranged along the collection axis, wherein the second quarter waveplate is arranged between the collection optics and the polarized beam splitter along the collection axis.

4. The optics arrangement as recited in claim 1, wherein the collector comprises at least one of a camera and a photodiode array.

5. The optics arrangement as recited in claim 1, further comprising source optics arranged along a source axis, wherein the source axis intersects the collection axis within the polarized beam splitter.

6. The optics arrangement as recited in claim 5, wherein the source axis is orthogonal relative to the collection axis.

7. The optics arrangement as recited in claim 5, wherein source optics include at least one of a collimating element and a diverging element.

8. The optics arrangement as recited in claim 1, further comprising an illuminator optically coupled to the polarized beam splitter along a source axis, wherein the source axis intersects the collection axis within the polarized beam splitter.

9. The optics arrangement as recited in claim 8, wherein the illuminator includes a polarized laser optically coupled to the beam splitter along the source axis.

10. The optics arrangement as recited in claim 8, wherein the illuminator includes an optical fiber with an endface, wherein the optical fiber endface is orthogonal or oblique relative to the source axis.

11. The optics arrangement as recited in claim 8, wherein the illuminator is arranged to provide light with a single polarization to the polarized beam splitter along the collection axis.

12. A retroreflector detector, comprising:
    an optics arrangement including;
        a polarized beam splitter arranged along an collection axis;
        a first quarter waveplate arranged along the collection axis;
        a second quarter waveplate arranged along the collection axis, wherein the second quarter waveplate is optically coupled to the first quarter waveplate by the polarized beam splitter to limit return of polarized illumination originating in a scene being illuminated for retroreflector detection;
    an illuminator arranged along a source axis, wherein the source axis intersects the collection axis within the polarized beam splitter; and
    a collector comprising a photodiode array arranged along the collection axis, wherein the second quarter waveplate is arranged between the collector and the polarized beam splitter.

13. The retroreflector detector as recited in claim 12, wherein the source axis is orthogonal relative to the collection axis, wherein source optics include at least one of a collimating element and a diverging element.

14. The retroreflector detector as recited in claim 12, wherein the illuminator includes an optical fiber with an endface, wherein the optical fiber endface is orthogonal or oblique relative to the source axis, and wherein the illuminator is arranged to provide light with a single polarization to the polarized beam splitter along the collection axis.

15. An imaging method, comprising:
receiving polarized illumination;
transmitting the polarized illumination along a collection axis through first and second quarter waveplates optically coupled by a polarized beam splitter, wherein the polarized illumination is received at the first quarter waveplate prior to being transmitted by the polarized beam splitter;
flipping polarization of the polarization of the received illumination during transmission through one of the first and second quarter waveplates; and
receiving broadband illumination through the first quarter waveplate at the polarized beam splitter, and attenuating the broadband illumination with the polarized beam splitter.

16. The method as recited in claim 15, wherein the polarized illumination is received at the polarized beam splitter prior to being transmitted through the first and second quarter waveplates.

17. An imaging method, comprising:
receiving polarized illumination;
transmitting the polarized illumination along a collection axis through first and second quarter waveplates optically coupled by a polarized beam splitter;
flipping polarization of the polarization of the received illumination during transmission through one of the first and second quarter waveplates, wherein the polarized illumination is received at the first quarter waveplate prior to being transmitted by the polarized beam splitter; and
reflecting polarized illumination at an angle oblique relative to the collection axis.

* * * * *